United States Patent [19]

Chiang et al.

[11] Patent Number: 5,008,444

[45] Date of Patent: Apr. 16, 1991

[54] PROCESS FOR THE PRODUCTION OF SUBSTITUTED ACRYLOYLOXYHYDROXYPROPYL-TRIALKYLAMMONIUM CHLORIDE

[75] Inventors: William G. Chiang, Fayetteville; Richard M. Jobbins, Marcellus; Michael P. Popule, Syracuse, all of N.Y.

[73] Assignee: Polypure, Inc., Solvay, N.Y.

[21] Appl. No.: 456,340

[22] Filed: Dec. 26, 1989

Related U.S. Application Data

[63] Continuation-in-part of Ser. No. 278,297, Nov. 30, 1988, abandoned, and a continuation-in-part of Ser. No. 278,299, Nov. 30, 1988, abandoned, and a continuation-in-part of Ser. No. 278,300, Nov. 30, 1988, abandoned.

[51] Int. Cl.$^5$ .............................................. C07C 69/52
[52] U.S. Cl. .................................. 560/222; 560/209; 560/223
[58] Field of Search ............... 526/292.2; 560/209, 560/223, 222

[56] References Cited

U.S. PATENT DOCUMENTS

| | | | |
|---|---|---|---|
| 3,059,024 | 10/1962 | Goldberg et al. | 260/486 |
| 3,321,649 | 5/1967 | De Benedictis et al. | 526/291 |
| 3,329,706 | 7/1967 | Sobolev | 560/222 |
| 3,397,227 | 8/1968 | Sobolev | 560/209 |
| 4,169,208 | 9/1979 | Kametani et al. | 566/222 |
| 4,374,206 | 2/1983 | MacDonald et al. | 521/38 |

FOREIGN PATENT DOCUMENTS

| | | |
|---|---|---|
| 1593421 | 8/1966 | Fed. Rep. of Germany . |
| 1112912 | 8/1965 | United Kingdom . |
| 1140520 | 7/1966 | United Kingdom . |

OTHER PUBLICATIONS

170237x C.A., Sep. 28, 1972.
41973u C.A., May 16, 1973.

*Primary Examiner*—Joseph L. Schofer
*Assistant Examiner*—Alex H. Walker
*Attorney, Agent, or Firm*—Mathews, Woodbridge & Collins

[57] ABSTRACT

The preparation of 3-(R)acryloyloxy-2-hydroxypropyl-trialkylammonium halide monomer is enhanced by carrying out the reaction in a media which is a non-solvent for the monomer, but is a solvent for the reactants.

29 Claims, No Drawings

PROCESS FOR THE PRODUCTION OF SUBSTITUTED ACRYLOYLOXYHYDROXYPROPYLTRIALKYLAMMONIUM CHLORIDE

RELATED APPLICATIONS

This application is a continuation in part of applications Ser. No. 07/278,297, filed Nov. 30, 1988, now abandoned Ser. No. 07/278,299 filed Nov. 30, 1988, now abandoned and Ser. No. 07/278,300 filed Nov. 30, 1988, now abandoned.

BACKGROUND OF THE INVENTION

1. Field of the Invention

The present invention relates to a process for making 3-(2-substituted acryloyloxy)-2-hydroxypropyltrialkyl ammonium chloride and its isomer, 2-(2-substituted acryloyloxy)-3-hydroxypropyltrialkylammonium chloride, wherein the substituent is hydrogen or lower alkyl of 1 to 4 carbon atoms.

2. Description of the Prior Art

The quaternary salt 3-methacryloyloxy-2-hydroxypropyltrimethylammonium chloride and its isomer 2-methacryloyloxy-3-hydroxypropyltrimethylammonium chloride are generally referred to as MAHTAC.

MAHTAC is a cationic vinyl monomer which can be polymerized or copolymerized with a number of other vinyl monomers to produce polymers which are useful in antistatic, flocculation or sludge dewatering applications. If high molecular weight polymers are to be synthesized without gellation due to crosslinking, it is essential that the MAHTAC purity with regards to molecules with two or more vinyl groups be very high. It is also essential that the yield be high for economic viability.

A significant number of references detailing the synthesis of MAHTAC have appeared over the last 25 years. However, it appears that only limited production of this material has occurred and that it is not presently being manufactured commercially. It is likely that this production has not occurred because of low yields and/or low purity associated with the prior art.

U.S. Pat. Nos. 3,321,649; 3,329,706; and 3,428,617 teach that MAHTAC may be prepared by reacting methacrylic acid with an aqueous solution of glycidyltrimethylammonium chloride (GTAC). The reactions are carried out in a homogeneous aqueous solution. The product must be precipitated, extracted or recrystallized before it can be used to make useful polymers. This method also produces the hydrolysis product of GTAC which is present in the mixture as a methacrylate salt:

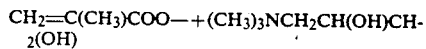

Separation of this salt from the desired product is difficult but if it is not removed, polymers made from the MAHTAC will be amphoteric and have reduced effectiveness due to intramolecular charge neutralization. U.S. Pat. No. 3,329,706 describes a process which produces purified MAHTAC in only 93% yield with a melting point of 176°-178° C. We have confirmed their Example 1 and produced MAHTAC with 70% yield and a melting point of only 176°-178° C.

Japanese Kokai 73/34,116 and 77/73,817 teach the synthesis of MAHTAC by reacting glycidylmethacrylate with trimethylamine hydrochloride. The synthesis is carried out in solvents such as alcohols, dimethylsulfoxide or sulfolane. Reaction products are separated by crystallization through cooling or the addition of a solvent such as acetone or cyclohexane. The references report yields of 78% or less and a melting point range of 180°-182° C. Japanese 73/34,116 also describes a method of reacting methacrylic acid and epihalohydrin to form a product which is then reacted with trimethylamine. They report that the reaction is very slow, polymerization losses can not be avoided and trimethylamine escapes from the reaction system. This reference teaches away from the use of the method.

U.S. Pat. No. 3,397,227 and British Patent 1,140,520 teach that MAHTAC may be prepared by treating methacrylic acid simultaneously with epihalohydrin and trimethylamine in an inert, polar solvent. The products of this reaction are separated by precipitation through the addition of a non-solvent, crystallization through a cooling procedure, or by selective extraction. The drawback of this process is the low yield; less than 83% based on trimethylamine and even lower based on the epihalohydrin and carboxylic acid. A major by-product, 3-chloro-2-hydroxypropyltrimethylammonium chloride, which comprises more that 25% of the reaction product has been identified in duplications of the patent examples.

Polish Patent 119,898 relates to a process for making MAHTAC by reacting methylmethacrylate with 3-chloro-2-hydroxyproplytrimethylammonium chloride (CHPTAC) in dimethylsulfoxide. The process involves distillation and separation. One drawback of this process is that the solubility of CHPTAC in the reaction medium is low, which leads to low reaction rates unless the other reactant is present in very high concentrations.

British Patent 1,112,912 and Belgian Patent 688,940 teach a method of producing MAHTAC by reacting potassium methacrylate with 3-chloro-2-hydroxypropyltrimethylammonium chloride in solvents such as acetonitrile or ethanol. In their Example 1, the reaction is carried out in acetonitrile. Potassium chloride is reported to precipitate from the reaction medium and is filtered. Tan colored MAHTAC with a broad melting range of 173°-180° C. is isolated by distilling off the acetonitrile. The MAHTAC then had to be recrystallized from a mixture of isopropanol and ethyl acetate. We have attempted to duplicate the results of this Example without success. Since the concentrations of potassium methacrylate and CHPTAC are not specifically defined in the case, we carried out reaction at three different concentrations The first one assumed that 1 part was one gram, the second 0.5 grams and the third 0.2 grams. In all cases the reaction was heterogeneous. Potassium methacrylate (PMA) and CHPTAC are only sparingly soluble in acetonitrile. This limits their concentrations in the reaction medium and keeps the reaction rate low. The products also have low solubility. The solubilities, in decreasing order are: PMA > MAHTAC > CHPTAC > KCl. At no point was it possible to separate KCl leaving behind a MAHTAC solution. It was not possible to simply separate MAHTAC uncontaminated by the other salts. MAHTAC yields were measured to be less than 51.1% and even after recrystallization from 1:1 isopropanol and ethyl acetate the purity was only 58.2%. The reaction conditions are presented in Example 7. It is possible that the experiments in these patents may have been contaminated with water or another agent which yielded an unverifiable result.

None of the above processes produce a high purity product in high yield. It is desirable to have a process which does both economically.

Accordingly, it is an object of this invention to provide a process for the preparation of 3-(2-substituted acryloyloxy)-2-hydroxypropyltrialkylammonium chloride monomers and their isomers, and more particularly, 3-methacryloyloxy-2-hydroxypropyltrimethylammonium chloride monomer and its isomer wherein, for a given reaction time, the yield is higher than in current processes and the purity of the product is higher.

It is another object of this invention to provide a process wherein crystalline monomers having greater particle size and/or molecular weights can be obtained. Still other objects of this invention will be apparent to those skilled in the art upon reference to the following detailed description and the claims.

SUMMARY OF THE INVENTION

In accordance with this invention, there is provided a process for preparing a 3-(R)acryloyloxy-2-hydroxypropyltrialkylammonium halide monomer comprising reacting the halohydroxypropyl ester of an acid of the formula $CH_2=C(R)COOH$ wherein R is selected from the group consisting of hydrogen and alkyl of 1 to 4 carbon atoms with a trialkylamine at a temperature and for a time sufficient to form 3-(R)acryloyloxy-2-hydroxypropyltrialkylammonium halide and its isomer, 2-(R)acryloyloxy-3-hydroxypropyltrialkylammonium halide, wherein said reaction occurs in a non-solvent for said 3-(R)acryloyloxy-2-hydroxypropyltrialkylammonium halide and its isomer and the molar ratio of said halohydroxypropyl ester to said trimethylamine is about 1.0:1.0 to about 1.0:2.0.

Additional aspects of this invention include the optional use of a catalyst having an epoxy functional group, the charging of reaction product during the reaction to seed the reaction and forming the halohydroxypropyl ester starting reactant in a non-solvent for this ester.

The present invention provides a versatile process for the preparation of substituted acryloyloxy-2-hydroxypropyltrialkylammonium chloride which can also be referred to as 3-(R)acryloyloxy-2-hydroxypropyltrialkylammonium chloride and its isomer 2-(R)acryloyloxy-3-hydroxypropyltrialkylammonium chloride. In the foregoing the R group (or substituent) for acryloyloxy is either hydrogen or alkyl having 1 to 4 carbon atoms. The other alkyl group in the alkyl ammonium chloride also contains from 1 to 4 carbon atoms. For convenience, the invention will hereafter be referred to in terms of its most desirable product, namely 3-methacryloyloxy-2-hydroxypropyltrimethylammonium chloride and its isomer 2-methacryloyloxy-3-hydroxypropyltrimethylammonium chloride which will hereinafter be collectively referred to as MAHTAC. It will be readily apparent to those skilled in the art that by the selection of other substitutents, falling within the scope stated above, a number of other similar cationic vinyl monomers can be prepared.

The process of the present invention permits the synthesis of high purity MAHTAC in high yield without requiring special purifications or other treatments. The advantages of this invention are (1) the direct production of crystalline MAHTAC by carrying the reaction out in a solvent for the reactants and a non-solvent for MAHTAC; (2) the synthesis of MAHTAC at a commercially viable rate using an appropriate catalyst; and (3) the production of crystalline monomer of sufficient size to allow easy separation from the reaction medium.

In the process of this invention, 3-chloro-2-hydroxypropylmethacrylate and its isomer 2-chloro-3-hydroxypropylmethacrylate (collectively called CHPM) are reacted with anhydrous trimethylamine in a polar, aprotic solvent which is a good solvent for the reactants but a poor solvent for MAHTAC. As the reaction proceeds, the MAHTAC precipitates as a white crystal. This crystal is easily separated from the reaction solvent which contains the impurities of the reaction.

Synthesis of the CHPM has been detailed in patents and in several journals. It is also available as Sipomer ®CHPM from Alcolac, Inc. CHPM is made by reacting stoichiometric or nearly stoichiometric quantities of epichlorohydrin and methacrylic acid at temperatures from about 50° to 100° C. in the presence of a polymerization inhibitor and a catalyst. Catalysts may include amines, quaternary ammonium salts or any of a number of other compounds. Literature references teach purification by extraction of residual methacrylic acid with sodium bicarbonate, followed by acid and water washes and distillation. As a consequence of side reactions, the CHPM contains, among other impurities, from 0.1 to about 2.0% of 2-hydroxypropane-1,3-dimethacrylate (HPDMA) and 3-chloropropane-1,2-dimethacrylate (CPDMA). Both of these diesters are poorly removed by the CHPM purification procedure. Since they contain two double bonds, they are polymerization crosslinking agents. It is essential that they be reduced to levels below about 10 parts-per-million in any MAHTAC made from CHPM if the MAHTAC is to used in the synthesis of linear, high molecular weight polymers One advantage of the invention described herein is that CHPM purification steps are not required for the synthesis of MAHTAC with low diester levels.

In the process of this invention CHPM is made according to the literature references or is purchased. Additionally, CHPM is advantageously prepared by reacting methacrylic acid (MAA) and epichlorohydrin (EPI) in the presence of a mixture of 3-methacryloyloxy-2-hydroxypropyltrimethyl ammonium chloride and its isomer as catalyst in step (a). Commercially available methacrylic acid and epichlorohydrin may be used in the present invention. Preferably, the molar ratio of methacrylic acid used to epichlorohydrin is about 0.5:1.0 to 1.0:0.5. If the ratio of epichlorohydrin to methacrylic acid used exceeds 1.0:0.5, polyepichlorohydrin forms. More preferably, the molar ratio of methacrylic acid to epichlorohydrin is about 0.8:1.0 to about 1.0:0.8. Most preferably, the molar ratio of methacrylic acid to epichlorohydrin is about 0.9:1.0 to about 1.0:1.0. The use of a slight excess epichlorohydrin is most preferred.

It has been discovered that a mixture of 3-methacryloyloxy-2-hydroxypropyltrimethylammonium chloride monomer and its isomer is a catalyst with advantages over triethylamine (a catalyst used in the art) in the formation of the chlorohydrin esters in step (a) of the monomer preparation.

Preferably, the molar ratio of the mixture of 3-methacryloyloxy-2-hydroxypropyltrimethylammonium chloride monomer and its isomer to methacrylic acid is about 0.01:1.0 to about 0.2:1.0. More preferably, the molar ratio of the MAHTAC mixture to methacrylic acid is about 0.01:1.0 to about 0.1:1.0. Most preferably, the molar ratio of the MAHTAC mixture to methacrylic acid is about 0.02:1.0 to about 0.04:1.0.

The methacrylic acid and epichlorohydrin are reacted in the presence of the MAHTAC monomer and its isomer at a temperature and for a time sufficient to form a reaction product. Preferably, the methacrylic acid and epichlorohydrin are reacted in the presence of the MAHTAC mixture at a temperature of about 25° to about 100° C. More preferably, the temperature is about 50° to about 100° C.; most preferably, the temperature is about 65° to about 90° C. More preferably, the reaction time is about 3 to about 24 hours; most preferably, the reaction time is about 5 to about 7 hours. Reaction pressure should be about atmospheric.

Preferably, the reaction occurs in the presence of a polymerization inhibitor. Preferred polymerization inhibitors are p-methoxyphenol, hydroquinone and phenothiazine; these materials are available in commercial quantities. The polymerization inhibitors may be used in conventional amounts.

Although not wishing to be bound by theory, it is believed that the reaction mechanism of the step (a) synthesis involves formation of an intermediate ionic complex [catalyst-acid] and then insertion of the epichlorohydrin epoxy ring into the complex [ionic complex-epichlorohydrin] via trans-opening of the epoxide ring.

Purification of the CHPM solution before the conversion to MAHTAC is unnecessary. It has been found that although the use of a purified CHPM solution produces a high purity 3-methacryloyloxy-2-hydroxypropyltrimethylammonium chloride monomer, the overall process yield is lower and the reaction time is much longer than when an unpurified CHPM solution is used. If desired, crude CHPM solution can be purified to remove any residual methacrylic acid, epichlorohydrin and other impurities. To do this, the crude CHPM solution is first extracted with a saturated aqueous NaHCO$_3$ until the methacrylic acid is removed followed by vacuum distillation to remove any residual epichlorohydrin and other residual impurities.

One mole of CHPM and from 0.5 to 2 moles of anhydrous trimethylamine are added to sufficient solvent to form a solution containing from about 35 to 85% of the solvent. More preferably, the mole ratio of trimethylamine to CHPM is 1.0:1.0 to 1.2:1.0. The solvent is selected so that the reactants are readily soluble but the MAHTAC has a limited solubility. The solvent should also not enter into any reactions with the reactants or products. Polar protic solvents are unsatisfactory since they may lead to hydrolysis or transesterifications. Water and alcohols are not satisfactory for this reason. Preferred solvents include tetrahydrofuran, acetone, acetonitrile, propionitrile, butyronitrile, dimethylformamide, dimethylsulfoxide, methyl ethyl ketone, ethyl acetate, and 1,1,2-trichlorethene. More preferred solvents are acetonitrile, acetone, tetrahydrofuran, methyl ethyl ketone, ethyl acetate and 1,1,2-trichlorethene. The most preferred solvent is acetonitrile.

This solution is then allowed to react under its natural vapor pressure, or any convenient higher pressure, at a temperature of from 25° to about 95° C. More preferably, the temperature is from 45° to about 85° C. and most preferably from 50° to about 70° C. Preferably, the reaction time is from about 2 to 48 hours and more preferably, the reaction time is from 3 to about 25 hours.

Most preferably, the reaction time is from 4 to about 10 hours.

Preferably, the reaction is carried out in the presence of a polymerization inhibitor such as p-methoxyphenol, phenothiazine or hydroquinone. These materials are available commercially and are used in conventional amounts.

During the course of the reaction, MAHTAC precipitates as a white crystal. When the reaction is complete, the crystalline mass is separated from the reaction mixture by a conventional means; such as filtration or centrifugation. We have found centrifugation to be particularly effective. If desired, washing of the crystals may be done in the filter or the centrifuge to reduce the amount of "mother liquor" on the crystal surfaces. This reduces the impurities further.

It has been unexpectedly found that the rate of formation of MAHTAC can be accelerated by the presence of a component with an epoxy functional group. Although not wishing to be bound by theory, MAHTAC may be formed by at least two mechanisms. One is the direct alkylation of trimethylamine by chlorine containing functional group of the CHPM molecule yielding a quaternary ammonium chloride The second involves the formation of glycidylmethacrylate from CHPM which is then attacked by the nucleophilic trimethylamine. In the process, MAHTAC is formed and a new molecule of glycidylmethacrylate is generated from CHPM. This process is repeated over and over until the reactants are consumed or the reaction stopped. This reaction is much faster than the direct alkylation. The overall reaction follows the scheme:

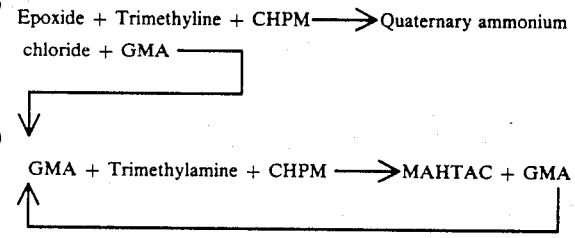

Many compounds with an epoxy functional group may react with trimethylamine to initiate this cycle. For example, a small amount of epichlorohydrin may react with the trimethylamine to yield glycidyltrimethylammonium chloride and in the process, one molecule of CHPM would be converted to GMA. Suitable compounds may be selected from the group

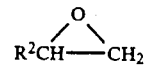

where $R^2$ is selected from the group consisting of hydrogen, an alkyl or alkenyl group of 1 to 10 carbon atoms, an alkaryl or aralkyl group of 7 to 11 carbons, amine or trimethylammonium ion. Other suitable compounds include, but are not limited to, glycidyl acrylate, glycidyl methacrylate (GMA), allyl glycidyl ether, glycidyl trimethylammonium chloride, propylene oxide and epichlorohydin. The higher the ratio of the epoxy containing "catalyst" to CHPM, the faster the reaction proceeds. Preferred ratios range from 0.001:1.0 to about 0.1:1.0. More preferably, the ratio is from 0.01:1.0 to 0.08:1.0.

Crystal purity is critical to the formation of linear high molecular weight polymers. In the reaction, impurities such as HPDMA and CPDMA are present due either to their presence in the CHPM or their formation during the course of the reaction with trimethylamine. They may result from the reaction of CHPM with residual methacrylic acid or from transesterifications. Other impurities which may be present include 1,3-bis(trimethylammonium)-2-hydroxypropane dichloride (DIQUAT); 2,3-dihydroxypropylmethacrylate; 2,3-dihydroxypropyltrimethylammonium chloride (DHPTAC) and methacrylic acid. These are not crosslinking agents and are not particularly detrimental to the formation of high molecular weight polymers even if present at levels of a few percent.

It has been reported that the rate of MAHTAC formation may be enhanced by the presence of quaternary ammonium salts. In addition we have found the presence of solid MAHTAC at the beginning of the reaction can increase the size of the crystals generated. Crystals with a size greater than about 40 microns have been found to be higher in purity (lower in CPDMA, HPDMA and residual starting material) and easier to separate from the reaction medium than smaller ones.

The following examples are included to illustrate the preparation of the compositions of the present invention, but are not to be considered limiting. Unless otherwise specified, all parts are parts by weight and all temperatures are expressed as degrees Celsius.

EXAMPLE 1

This example is directed to the synthesis of 3-chloro-2-hydroxypropylmethacrylate and its isomer.

To a 500 mL 3-necked, round bottom flask, equipped with a thermometer, air driven stirrer and reflux condenser, are charged 172.19 grams (2 moles) of methacrylic acid, 194.42 grams (2.1 moles) of epichlorohydrin, 0.88 grams of p-methoxyphenol (MEHQ) as a polymerization inhibitor, and 8.1 grams (0.08 moles) of triethylamine as a catalyst. The reaction mixture is heated to 85° C. for 5 hours. The yield is greater than 95% based on methacrylic acid. At the end of the reaction the following composition is measured by gas chromatography:

| Component | Weight Percent |
| --- | --- |
| CHPM & isomer | 88.41 |
| Epichlorohydrin | 0.90 |
| Methacrylic Acid | 0.73 |
| Dichloropropanol | 3.61 |
| GMA | 1.44 |
| HPDMA | 1.11 |
| MEHQ | 0.24 |
| Chloropropanediol | 0.25 |
| Triethylamine | 2.28 |
| DHPMA | 0.66 |
| CPDMA | 0.36 |

EXAMPLE 2

To a 500 mL, 3-necked, round bottom flask, equipped with a thermometer, air driven stirrer and reflux condenser, are charged 172.31 grams (2 moles) of methacrylic acid, 194.4 grams (2.1 moles) of epichlorohydrin, 0.86 grams of p-methoxyphenol (MEHQ) as a polymerization inhibitor, and 7.43 grams (0.04 moles) of benzyltriethylammonium chloride as a catalyst. The reaction mixture is heated to 85° C. and a significant exotherm was noted as the temperature approached 85° C. The temperature is then maintained at 85° C. for 5 hours. The yield is greater than 95%, based on methacrylic acid.

At the end of the reaction the following composition is, as measured by gas chromatography,:

| Component | Weight Percent |
| --- | --- |
| CHPM & isomer | 88.27 |
| Epichlorohydrin | 1.27 |
| Methacrylic Acid | 0.67 |
| Dichloropropanol | 3.97 |
| GMA | 0.68 |
| HPDMA | 1.22 |
| MEHQ | 0.24 |
| DHPMA | 0.95 |
| CPDMA | 0.18 |
| Catalyst | 2.55 |

EXAMPLE 3

The CHPM of Example 1 is purified by first extracting with saturated aqueous sodium bicarbonate to remove methacrylic acid followed by 2% sulfuric acid and water. After vacuum distillation, a light yellow CHPM solution with greater than 97% purity is obtained.

The product has the following composition (by gas chromatography):

| Component | Weight Percent |
| --- | --- |
| CHPM & isomer | 97.31 |
| Epichlorohydrin | 0.24 |
| Dichloropropanol | 0.81 |
| GMA | 0.07 |
| HPDMA | 0.40 |
| MEHQ | 0.81 |
| DHPMA | 0.36 |

EXAMPLE 4

This example demonstrates the synthesis of crystalline MAHTAC from the unpurified CHPM of Example 1.

To a 500 mL Fisher Porter pressure bottle equipped with a magnetic stirrer are charged 150.02 grams (0.743 mole) of CHPM from Example 1, 155.72 grams of acetonitrile, 0.25 grams of MEHQ and 48.4 grams (0.819 mole) of trimethylamine. The bottle is sealed and heated in an oil bath at 65° C. for 22 hours. The crystals began to precipitate after 45 minutes of reaction. The reaction mixture is filtered and dried through a Buchner funnel. The yield of MAHTAC is 93% of theory. Analysis of the crystals by liquid chromatography showed that they are 95.8% MAHTAC, 1.9% DHPTAC and 2.3% DIQUAT. The melting point is 180°-182° C.

EXAMPLE 5

This example demonstrates the synthesis of crystalline MAHTAC from the unpurified CHPM OF Example 2.

To a 500 mL Fisher Porter pressure bottle equipped with a magnetic stirrer, are charged 150.03 grams (0.746 mole) of CHPM from Example 2, 154.05 grams of acetonitrile, 0.2 grams of MEHQ and 49.5 grams (0.837 mole) of trimethylamine. The bottle is sealed and heated in an oil bath at 65° C. for 10 hours. The solution began to turn cloudy after 30 minutes of reaction. The reaction mixture is filtered and dried through a Buchner funnel.

The yield of MAHTAC is 98.2% of theory. Analysis of the crystals by liquid chromatography showed they are 94.9% MAHTAC, 1.9% DHPTAC AND 3.2% DIQUAT. The melting point is 180°–182° C.

EXAMPLE 6

To a 500 mL Fisher Porter pressure bottle equipped with a magnetic stirrer are charged 100.12 grams (0.5454 mole) of purified CHPM from Example 3, 100.12 grams of acetonitrile, 0.22 grams of MEHQ and 35.9 grams (0.607 mole) of trimethylamine. The bottle is sealed and heated in an oil bath at 65° C. for 25 hours. The solution began to turn cloudy after 30 minutes of reaction. The reaction mixture is filtered and dried through a Buchner funnel. The yield of MAHTAC is 93.3% of theory. Analysis of the crystals by liquid chromatography showed they are 98% MAHTAC, 2% DHPTAC and essentially no DIQUAT. The melting point was 181°–183° C.

EXAMPLE 7

This example demonstrates that the process of this invention differs significantly from that of British Patent 1,112,912. In Example 1 of '912, the manufacture of 3-methacryloyloxy-2-hydroxypropyltrimethylammonium chloride from the reaction of potassium methacrylate (PMA) and 3-chloro-2-hydroxypropyltrimethylammonium chloride (CHPTAC) is disclosed. The MAHTAC is synthesized in a 500 mL 3-neck flask fitted with a thermometer, stirrer and a reflux condenser. Into the flask are placed 18.8 parts CHPTAC, 12.4 parts of PMA, 200 mL of acetonitrile and 0.01 parts of MEHQ as a polymerization inhibitor. The reaction mixture is heated under reflux for 2.5 hours and then allowed to stand at room temperature overnight. The reaction mixture is filtered to remove 7.72 parts of potassium chloride. The acetonitrile is distilled from the filtrate under reduced pressure, leaving as a residue 22.0 parts (93% of theory) of MAHTAC product. The crude MAHTAC product is purified by recrystallization from a 1:1 mixture of isopropanol and ethyl acetate.

The experiment essentially as described is repeated but with very different results. Since no weight unit is given for the reacting components, three experiments are done with one part taken as 1.0 gram, 0.5 gram and 0.2 gram and 0.2 gram. The reaction conditions are described in Table I below.

TABLE I

| Experiment Number | Reaction Mixture | Weight (g) | Moles | Reaction Hrs. | Yield % |
|---|---|---|---|---|---|
| A | PMA | 12.42 | 0.10 | 2.5 | 51.1 |
|   | CHPTAC | 18.91 | 0.10 |   |   |
|   | MEHQ | 0.01 |   |   |   |
|   | CH₃CN | 155.2 |   |   |   |
| B | PMA | 6.28 | 0.05 | 2.5 | 44.8 |
|   | CHPTAC | 9.48 | 0.05 |   |   |
|   | MEHQ | 0.01 |   |   |   |
|   | CH₃CN | 155.10 |   |   |   |
| C | PMA | 2.47 | 0.02 | 2.5 | 47.4 |
|   | CHPTAC | 3.74 | 0.02 |   |   |
|   | MEHQ | 0.01 |   |   |   |
|   | CH₃CN | 155.10 |   |   |   |

All reactions are heterogeneous and the purity of the MAHTAC after recrystallization is 49.1, 58.2, and 47.9 for experiments A, B and C, respectively.

Examples 8 through 11 demonstrate that the rate of formation of MAHTAC can be greatly enhanced by the addition of an epoxy containing compound to the reaction mixture. The experimental results are presented in Table II below.

EXAMPLE 8

This example shows the rate of MAHTAC formation when no epoxy compounds are present in the reaction mixture. As shown in Table II, only 33.3% of the CHPM is converted to MAHTAC in three hours at 65° C. when no glycidylmethacrylate was present. The product purity is 97.9%.

EXAMPLE 9

When 1.09% GMA is present in the reaction mixture, 69.1% of the CHPM formed MAHTAC in three hours. This is a significant rate enhancement over Example 8. The product purity is 98.6%.

EXAMPLE 10

When 3.27% GMA is present in the reaction mixture, 98.6% of the CHPM is converted to MAHTAC in three hours. This is a further improvement over Example 9. The MAHTAC purity is 97.9%.

EXAMPLE 11

This example shows that the rate enhancement is also seen at 45° C. A three hour CHPM conversion of 54.3% is found and the product is 98.3% pure.

TABLE II

|  | Ex. 8 | Ex. 9 | Ex. 10 | Ex. 11 |
|---|---|---|---|---|
| Reactants (g) |  |  |  |  |
| CHPM | 100.12 | 100.13 | 100.14 | 100.15 |
| TMA | 35.9 | 35.3 | 35.7 | 35.7 |
| CH₃CN | 100.12 | 99.05 | 96.83 | 96.81 |
| MEHQ | 0.22 | 0.22 | 0.23 | 0.22 |
| GMA | 0.0 | 1.09 | 3.27 | 3.28 |
| Conditions |  |  |  |  |
| Temperature (°C.) | 65 | 65 | 65 | 45 |
| Conversion at 3 Hrs. | 33.27 | 69.08 | 98.62 | 54.29 |
| Reaction time (Hrs) | 25 | 7 | 3 | 7 |
| Product |  |  |  |  |
| Crystal Wt (g) | 93.04 | 106.4 | 121.2 | 124.4 |
| Yield (%) | 87.23 | 91.7 | 98.32 | 97.87 |
| MAHTAC purity (%) | 97.94 | 98.61 | 97.93 | 98.3 |

EXAMPLE 12

Table III below shows that the same rate enhancement effect may be achieved by substituting another epoxide for GMA. In this example, equivalent molar amounts of GMA and glycidyl allyl ether (GAE) are used in two essentially identical reactions. The results are very similar, and many other epoxides may be suitable for enhancing the reaction rate.

TABLE III

|  | Ex. 12 | Ex. 13 |
|---|---|---|
| Reactants (g) |  |  |
| CHPM | 100.15 | 100.10 |
| TMA | 36.4 | 38.7 |
| CH₃CN | 96.84 | 97.41 |
| MEHQ | 0.21 | 0.21 |
| GMA | 3.25 | 0.0 |
| GAE | 0.0 | 2.69 |
| Total Wt. | 236.85 | 239.11 |
| Conditions |  |  |
| Temperature (°C.) | 65 | 65 |
| Conversion at 3 Hrs. | 97.09 | 98.27 |
| Reaction time (Hrs.) | 3.5 | 3.5 |
| Product |  |  |
| Crystal Wt (g) | 114.16 | 120.8 |

TABLE III-continued

|  | Ex. 12 | Ex. 13 |
| --- | --- | --- |
| Yield (%) | 88.44 | 93.57 |
| MAHTAC purity (%) | 95.23 | 96.77 |

EXAMPLE 13

This Example is directed to the preparation of 3-chloro-2-hydroxyproppylmethacrylate (CHPM).

To a 500 mL. 3-necked round bottomed flask, equipped with a thermometer, agitator and reflux condenser, are charged 172.3 grams (2 moles) of methacrylic acid (MAA), 194.40 grams (2.1 moles) of epichlorohydrin (EPI), 0.86 gram (0.5 weight % of MAA) of p-methoxyphenol as polymerization inhibitor and 9.52 grams (0.04 mole) of 3-methacryloyloxy-2-hydroxypropyltrimethylammonium chloride as catalyst. The reaction mixture is heated to 85° C. for 7 hours. A slight exotherm is observed in the first hour of the reaction. The yield of the CHPM is 95% based on methacrylic acid and the purity of the CHPM was about 88.27%. Gas chromatographic analysis shows that the CHPM solution has the following composition (weight percent): CHPM 88.27%, EPI 1.27%, MAA 0.67% DCP 3.97%, GMA 0.68%, HPDMA 1.22%, MEHQ 0.24%, CPDMA 0.18%, DHPMA 0.95%, and catalyst 2.55%.

The crude CHPM solution is then extracted with a saturated aqueous $NaHCO_3$ until the disappearance of acid reaction (to remove residual methacrylic acid), then with a 2% sulfuric acid, and after that with water. After vacuum distillation to remove residual epichlorohydrin and water, a light yellow CHPM solution with greater than 97% purity is obtained.

EXAMPLES 14–16

Examples 14–16 are directed to the preparation of 3-chloro-2-hydroxypropylmethacrylate (CHPM).

The procedure of Example 13 is repeated under the conditions shown in Table IV below. Each reaction is conducted in the presence of 0.43 gram (0.5 weight % of MAA) of p-methoxyphenol. In order to minimize exothermic reaction, the reaction temperature at the first hour is kept at 65° C. and then gradually raised to 75° C. The yield of the CHPM is calculated. The reaction rate constant (K) in each Example is the slope of the plot of $-\ln([MAA]/[MAA_0])$ vs reaction time. The results are in Table IV below.

TABLE IV

| EX | $[EPI_0]/[MAA_0]$ | $[MAHTAC]/[MAA_0]$ | Temp. °C. | Time (Hrs) | K | Percent Yield |
| --- | --- | --- | --- | --- | --- | --- |
| 14 | 1.05 | 0.02 | 75 | 7 | 0.3179 | 97 |
| 15 | 1.05 | 0.03 | 75 | 6 | 0.4581 | 99 |
| 16 | 1.05 | 0.04 | 75 | 5 | 0.5287 | 97 |

Plotting $[MAHTAC]/[MAA_0]$ against K indicates that K in the formation of CHPM is a linear function of the MAHTAC catalyst concentration.

EXAMPLE 17

This Example is directed to the preparation of 3-methacryloyloxy-2-hydroxypropyltrimethylammonium chloride.

To a 500 mL. Fisher & Porter pressure bottle equipped with a magnetic stirrer are charged 150.03 grams (0.746 mole) of unpurified CHPM solution from Example 2, 154.05 grams of acetonitrile, 0.12 gram of p-methoxyphenol, and 49.5 grams (0.837 mole) of trimethylamine. The bottle is sealed and heated in an oil bath at 65° C. for 10 hours. The reaction mixture starts to turn cloudy after 30 minutes of stirring. A white crystalline MAHTAC monomer is obtained with a 98% yield. The average particle size of MAHTAC monomer product is 30 to 40 microns Liquid Chromatographic analysis shows that the white crystal is a composition of 94.9% of MAHTAC monomer, 3% of 2-hydroxypropane-1,3-bistrimethylammonium chloride (DIQUAT), and less than 1.9% of 2,3-dihydroxypropyltrimethylammonium chloride (DHPTAC). Other impurities determined by liquid chromatography of ether extracts are MAA 12 ppm., GMA 18 ppm., CHPM 350 ppm., DHPMA 87 ppm., and HPDMA 2244 ppm.

EXAMPLE 18

This Example illustrates the seeding effect of the MAHTAC monomer in the second step of the MAHTAC monomer preparation.

A procedure similar to that of Example 17 is followed. During the course of quaternization, a small amount of fine MAHTAC crystals in an amount of 5 weight % of CHPM is added into the batch liquor (super saturated solution). It is found that the average particle size of crystals increases to 200 microns and impurity levels dropped by a factor of four.

EXAMPLE 19

This example demonstrates the high purity of MAHTAC made by the process of the present invention. The following two experiments were carried out in an agitated, 7-liter, stainless steel, jacketed, pressure reactor, fitted with temperature and pressure instrumentation.

Experiment A

To the above reactor are added 400 grams of MAHTAC, 1500 grams of CHPM, 2600 grams of acetonitrile and 500 grams of trimethylamine. The reactor is heated to 50° C. and allowed to react for 19.5 hours. The contents of the reactor are then added to a 12 inch diameter, perforate basket centrifuge containing a Teflon TM filter cloth and separated from the mother liquor (ML) at 1960 rpm. They are then washed with 330 grams of acetonitrile at low speed followed by spinning again at 1960 rpm. The crystals are viewed under the microscope and found to have a mean size of 57.8 microns. The impurity levels for both the mother liquor and the washed crystals are listed in Table V below.

Experiment B

To the above reactor are added 120 grams of glycidyl methacrylate, 1500 grams CHPM, 2600 grams acetonitrile and 500 grams TMA. The reactor is heated to 50° C. for 5 hours. Following the procedure in the above experiment the reactor contents are centrifuged and washed. Microscopic examination of the crystals showed that they had a mean particle size of 16.5 microns. The impurity levels are listed in Table V below.

TABLE V

| Impurity | Experiment A (Large Crystal) | | Experiment B (Small Crystal) | |
| --- | --- | --- | --- | --- |
|  | ML (%) | (ppm) | ML (%) | (ppm) |
| DHPMA | 0.21 | 2.5 | 0.27 | 5.0 |
| MAA | 0.38 | 0.5 | 0.62 | 1.5 |
| CHPM | 1.6 | 28 | 1.2 | 95 |
| GMA | 1.2 | ND | 4.6 | 44 |
| HPDMA | 2.3 | 22 | 1.2 | 50 |

TABLE V-continued

| | Experiment A (Large Crystal) | | Experiment B (Small Crystal) | |
|---|---|---|---|---|
| Impurity | ML (%) | (ppm) | ML (%) | (ppm) |
| CPDMA | 4.9 | 35 | 4.8 | 130 |
| GTMA | 0.76 | 12 | 0.78 | 35 |

Table V shows the levels of the impurities found in the crystal mother liquor and in the washed crystal for the two experiments of Example 19. These experiments shown that a significant reduction (up to 73%) in crosslinking impurities can be achieved by increasing the crystal size from 16.5 to 57.8 microns.

Having described the invention in detail and by reference to preferred embodiments thereof, it will be apparent that modifications and variations are possible without departing from the scope of the invention defined in the appended claims.

The embodiments of the invention in which an exclusive property or privilege is claimed are defined as follows:

1. A process for preparing a 3-(R)acryloyloxy-2-hydroxypropyltrialkylammonium halide monomer comprising:
   reacting the halohydroxypropyl ester of an acid of the formula $CH_2=C(R)COOH$ wherein R is selected from the group consisting of hydrogen and alkyl of 1 to 4 carbon atoms with from 0.05 to 2.0 moles of a trialkylamine per mole of halohydroxypropyl ester at from about 25° to about 70° C. for a time sufficient to form 3-(R) acryloyloxy-2-hydrocypropyltrialkylammonium halide and its isomer, 2-(R)acryloylocy-3-hydroxypropyltrialkylammonium halide, wherein said reaction occurs in from about 35 85% of a non-solvent for said 3-(R)acryloyloxy-2-hydroxypropyltri-alkylammonium halide and its isomer;
   precipitating the halide monomer as the reaction proceeds.

2. The process of claim 1 wherein said reaction is carried out at a temperature of about 25° to about 90° C.

3. The process of claim 2 wherein in said temperature is about 50° to about 85° C.

4. The process of claim 1 wherein said non-solvent is selected from the group consisting of acetonitrile; acetone; methyl ethyl ketone; tetrahydrofuran; ethylacetate and 1,1,2-trichloroethene.

5. The process of claim 4 wherein said non-solvent is acetonitrile.

6. The process of claim 1 wherein said reaction occurs in the presence of a polymerization inhibitor.

7. The process of claim 1 wherein a catalyst is used, the molar ratio of said chlorohydroxypropyl ester to said catalyst is about 1.0:0.001 to about 1.0:0.1.

8. The process of claim 1 wherein the compound with an epoxy functional group is present in an amount from about 1.0:0.01 to about 1.0:0.08.

9. The process of claim 1 wherein a compound with an epoxy functional group is used, the molar ratio of said chlorohydroxypropyl ester to said compound is about 1.0:0.001 to about 1.0:0.1.

10. The process of claim 9 wherein the compound with an epoxy functional group is an epoxy having the formula:

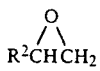

wherein $R^2$ is selected from the group consisting of hydrogen, alkyl of 1 to 10 carbon atoms, alkenyl of 1 to 10 carbon atoms, aldaryl of 7 to 11 carbon atoms, aralkyl of 7 to 11 carbon atoms, amine and trimethylammonium ion.

11. The process of claim 9 wherein the compound with an epoxy functional group is selected from the group consisting of glycidyl methacrylate, allyl glycidyl ether, glycidyl acrylate, glycidyl trimethylammonium chloride, propylene oxide and epichlorohydrin.

12. The process of claim 7 wherein the catalyst is 3-(R)acryloyloxy-2-hydroxypropyltrialkylammmonium chloride and its isomer.

13. The process of claim 12 wherein the catalyst is 3-methacryloyloxy-2-hydroxypropyltrimethylammonium chloride and its isomer.

14. The process of claim 1 wherein the halohydroxypropyl ester is prepared by reacting methacrylic acid and epichlorohydrin in the presence of a mixture of 3-methacryloyloxy-2-hydroxypropyltrimethylammonium chloride monomer and its isomer, 2-methacryloyloxy-3-hydroxypropyltrimethylammonium chloride monomer as catalyst at a temperature and for a time sufficient to form said ester.

15. The process of claim 14 wherein the molar ratio of said methacrylic acid to said epichlorohydrin is about 0.5:1.0 to about 1.0:0.5.

16. The process of claim 14 wherein the molar ratio of said mixture of 3-methacryloyloxy-2-hydroxypropyltrimethylammonium chloride monomer and its isomer to said methacrylic acid is about 0.01:1.0 to about 0.2:1.0.

17. The process of claim 14 wherein the reaction of methacrylic acid and epichlorohydrin is carried out at a temperature of about 25° to about 100° C.

18. The process of claim 14 wherein the reaction of methacrylic acid and epichlorohydrin is carried out in the presence of a polymerization inhibitor.

19. The process of claim 1 wherein the trialkylamine is trimethylamine.

20. The process of claim 1 further comprising the step of separating the precipitated halide monomer from the reaction non-solvent.

21. The process of claim 20 further comprising the step of washing the precipitated halide monomer.

22. The process of claim 1 further comprising the step of adding solid 3-(R) acryloyloxy-2-hydroxypropyltrialkylammonium halide monomer at the beginning of the reaction.

23. The process as recited in claim 1 wherein the molar ratio of said halohydroxypropyl ester to said trimethylamine is about 1.0:1.0 to about 1.0:2.0.

24. A process for preparing a 3-(R)acryloyloxy-2-hydroxypropyltrialkylammonium halide monomer comprising:
   reacting the halohydroxypropyl ester of an acid of the formula $CH_2=C(R)COOH$ wherein R is selected from the group consisting of hydrogen and alkyl of 1 to 4 carbon atoms with from 0.5 to 2.0 moles of a trialkylamine ester per mole of halohydroxypropyl at a temperature and for a time sufficient to form 3-(R)acryloyloxy-2-hydroxypropyltrialkylammonium halide and its isomer, 2-(R)a- cryloyloxy-3-hydroxypropyltrialkylammonium halide, wherein said reaction occurs in a non-solvent for said 3-(R)acryloyloxy-2-hydroxypropyltrialkylammonium halide and its isomer;

precipitating the halide monomer as the reaction proceeds to attain a yield of at least about 87%.

25. The process as recited in claim 24 wherein the yield attained is greater than 93%.

26. The process as recited in claim 24 wherein the molar ratio of said halohydroxypropyl ester to said trimethylamine is about 1.0:1.0 to about 1.0:2.0.

27. The process as recited in claim 24 wherein the purity is greater than about 95%.

28. A process for preparing a 3-(R)acryloyloxy-2-hydroxypropyltrialkylammonium halide monomer comprising:

reacting the halohydroxypropyl ester of an acid of the formula $CH_2=C(R)COOH$ wherein R is selected from the group consisting of hydrogen and alkyl of 1 to 4 carbon atoms with from 0.5 to 2.0 moles of a trialkylamine per mole of halohydroxypropyl ester at a temperature and for a time sufficient to form 3-(R)acryloyloxy-2-hydroxypropyltrialkylammonium halide and its isomer, 2-(R)acryloyloxy-3-hydroxypropyltrialkylammonium halide, wherein said reaction occurs in a non-solvent for said 3-(R)acryloyloxy-2-hydroxypropyltrialkylammonium halide and its isomer;

precipitating the halide monomer as the reaction proceeds to attain less than about 70 ppm of crosslinking agents.

29. The process as recited in claim 28 wherein there is less than about 10 ppm of crosslinking agents.

* * * * *

Disclaimer 5,008,444 — William G. Chiang, Fayetteville; Richard M. Jobbins, Marcellus; Michael P. Popule, Syracuse, all of N.Y. PROCESS FOR THE PRODUCTION OF SUBSTITUTED ACRYLOYLOXYHYDROXYPROPYLTRIALKYLAMMONIUM CHLORIDE. Patent dated April 16, 1991. Disclaimer filed March 10, 1997, by the assignee, S.N.F.

Hereby enters this disclaimer to all claims of said patent.
*(Official Gazette,* April 29, 1997)